United States Patent
Wang et al.

(10) Patent No.: US 11,596,319 B2
(45) Date of Patent: Mar. 7, 2023

(54) HEART RATE MODULE

(71) Applicant: GOERTEK INC., Shandong (CN)

(72) Inventors: Wentao Wang, WeiFang (CN); Bo Fu, WeiFang (CN); Xinliang Li, WeiFang (CN)

(73) Assignee: WEIFANG GOERTEK MICROELECTRONICS CO., LTD., Weifang (CN)

( * ) Notice: Subject to any disclaimer, the term of this patent is extended or adjusted under 35 U.S.C. 154(b) by 481 days.

(21) Appl. No.: 16/632,165

(22) PCT Filed: Sep. 6, 2018

(86) PCT No.: PCT/CN2018/104357
§ 371 (c)(1),
(2) Date: Jan. 17, 2020

(87) PCT Pub. No.: WO2019/232954
PCT Pub. Date: Dec. 12, 2019

(65) Prior Publication Data
US 2020/0229721 A1     Jul. 23, 2020

(30) Foreign Application Priority Data
Jun. 4, 2018 (CN) .......................... 201820858479.6

(51) Int. Cl.
*A61B 5/1455* (2006.01)
*A61B 5/024* (2006.01)
(52) U.S. Cl.
CPC .. *A61B 5/02427* (2013.01); *A61B 2562/0238* (2013.01); *A61B 2562/046* (2013.01)

(58) Field of Classification Search
CPC . A61B 5/024; A61B 5/02416; A61B 5/02427; A61B 5/02433; A61B 5/02444;
(Continued)

(56) References Cited

U.S. PATENT DOCUMENTS 5,305,744 A * 4/1994 Pfeiffer ................ A61B 5/1459
600/342
5,893,364 A * 4/1999 Haar .................. A61B 5/14552
600/310
(Continued)

FOREIGN PATENT DOCUMENTS

CN     104051448 A     9/2014
CN     204445866 U     7/2015
(Continued)

*Primary Examiner* — Chu Chuan Liu
(74) *Attorney, Agent, or Firm* — Holzer Patel Drennan

(57) ABSTRACT

A heart rate module, comprising a housing structure composed of a rear housing (2) and a light-transmitting cover plate (3), the housing structure being internally provided with a PCB assembly (1); the PCB assembly (1) comprises a PCB, PDs (6, 7) and an LED (5), the PDs (6, 7) and the LED (5) being fixed on the PCB according to a preset distance; a hot melt positioning column (21) is provided on the rear housing (2), and the PCB assembly (1) is fixed, by means of the hot melt positioning column (21), on the rear housing (2). Use of the heart rate module can solve the problems of the assembly method of the available heart rate meter being complicated and the requirement for a terminal product being high.

5 Claims, 3 Drawing Sheets

(58) Field of Classification Search
CPC .............. A61B 5/02438; A61B 5/1455; A61B 5/14551; A61B 5/14552; A61B 5/0205; A61B 5/14532; A61B 2562/02; A61B 2562/0233; A61B 2562/046; A61B 2562/0238
See application file for complete search history.

(56) References Cited

U.S. PATENT DOCUMENTS

| | | | | |
|---|---|---|---|---|
| 2004/0193063 | A1* | 9/2004 | Kimura | A61B 5/02416 600/500 |
| 2014/0168647 | A1* | 6/2014 | Ju | G08B 17/107 29/527.1 |
| 2014/0361147 | A1* | 12/2014 | Fei | A61B 5/1455 250/206 |
| 2015/0057511 | A1* | 2/2015 | Basu | A61B 5/14552 600/323 |
| 2016/0029911 | A1 | 2/2016 | Lee | |

FOREIGN PATENT DOCUMENTS

| | | |
|---|---|---|
| CN | 106073737 A | 11/2016 |
| CN | 107820410 A | 3/2018 |
| CN | 108078549 A | 5/2018 |

* cited by examiner

HEART RATE MODULE

TECHNICAL FIELD

The present application relates to a technical filed of a heart rate device, and more particularly, to a general heart rate module.

BACKGROUND ART

Most of the heart rate meters currently on the market come in two forms: one is a small heart rate device only with integrated PD (photodiode) and LED (light emitting diode); and the other form is to mount the PD and the LED onto a FPC soft board and a PCB hard board of a product separately, adjust the left-right spacing of the PD and LED, and the up-down spacing of the PD and LED from the LENS. Such two assembly manners are complicated, terminal products are required to make fine structural spacing to match the adjustment, and at the same time, terminal customers are required to separately develop algorithm writing, which has higher requirements for the terminal customers.

To solve the above problems, the present application provides a heart rate module.

SUMMARY

In view of the above problems, an object of the present application is to provide a heart rate module to solve the problems that the assembly ways of the existing barometers are complicated and the requirements for the terminal products are high.

The present application provides a heart rate module which comprises a housing structure composed of a rear housing and a light-transmitting cover plate, wherein a PCB assembly is disposed in the housing structure, the PCB assembly includes a PCB, a PD and an LED, wherein the PD and the LED are fixed on the PCB at a preset distance, a hot melt positioning column is disposed on the rear housing, and the PCB assembly is fixed on the rear housing through the hot melt positioning column.

In addition, a preferred configuration is that the PCB assembly further comprises a micro-control electronic device.

In addition, a preferred configuration is that a locating hole is provided on the PCB and corresponds to the hot melt positioning column on the rear housing.

In addition, a preferred configuration is that a plurality of through-slots are provided on the rear housing, wherein each of the plurality of through-slots is used to accommodate the PD or the LED, and grating baffles for preventing light interferences are respectively formed between the through-slots.

In addition, a preferred configuration is that a terminal locating hole is further provided on the rear housing, wherein the terminal locating hole is used for fixing and assembling with a terminal product.

In addition, a preferred configuration is that a black silk screen is provided in an area other than a position corresponding to that of the PD and the LED, on a surface of the light-transmitting cover plate, thereby forming a light-transmitting window at the position corresponding to that of the PD and the LED.

In addition, a preferred configuration is that the light-transmitting cover plate is fixed to the rear housing by a double-sided adhesive.

According to the above technical solution, in the heart rate module of the present application, the PCB assembly, the rear housing and the light-transmitting cover plate are assembled into a module, and the module pre-sets the distances of the PD, the LED and the light-transmitting cover plate and is assembled into a semi-finished product, the terminal customers can directly assemble the module into a product, thereby improving the efficiency and yield of terminal customer design and production line assembly.

BRIEF DESCRIPTION OF THE DRAWINGS

Other objects and results of the present application will be more apparent and easily to understand with the reference to the following description in conjunction with the drawings with a more comprehensive understanding of the present application. In the drawings.

REFERENCE NUMERAL

Figure 1:
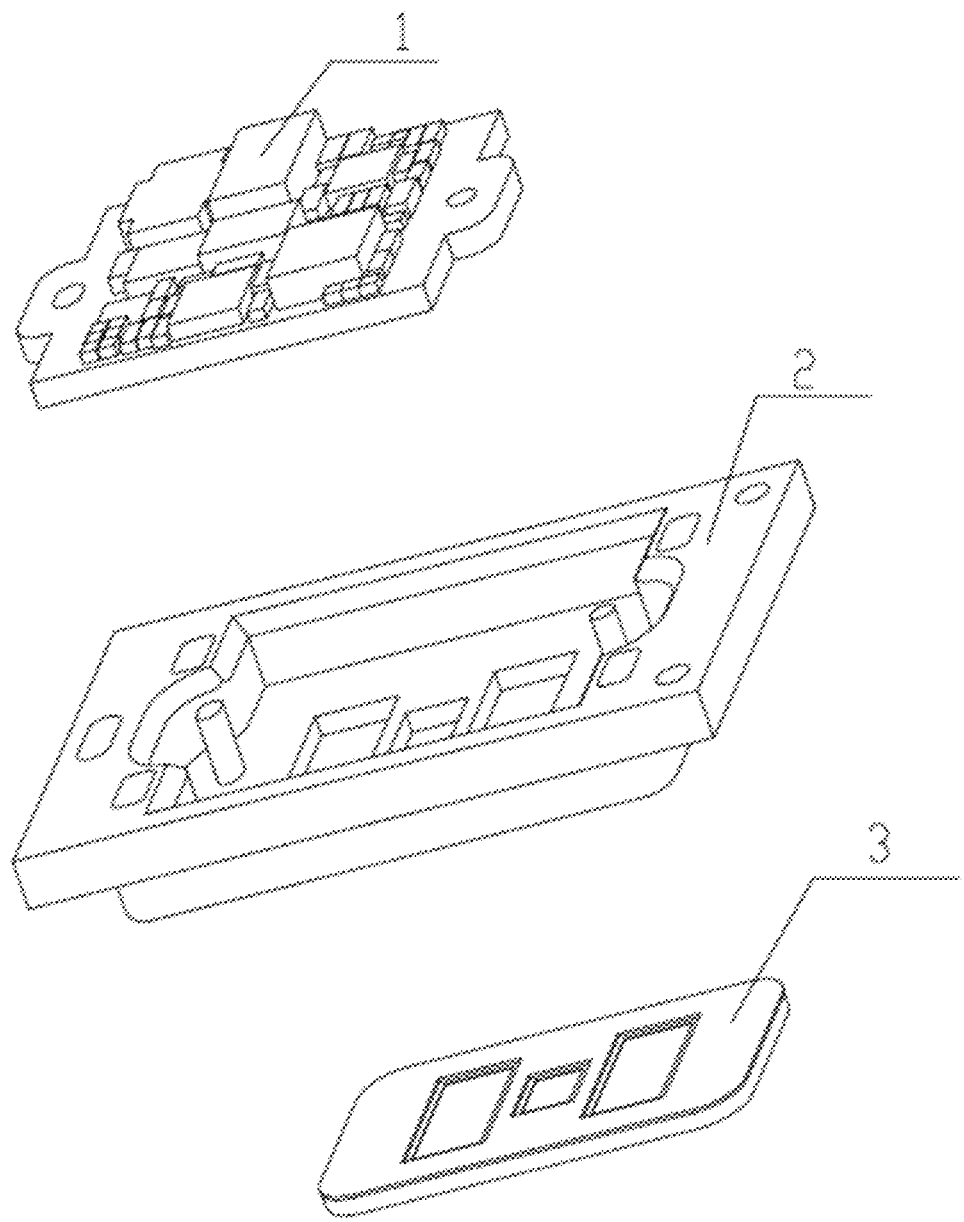
FIG. 1 is a exploded structural schematic diagram of the heart rate module according to the embodiment of the present application.

1: PCB assembly, 2: rear housing, 3: light-transmitting cover plate, 4: double-sided adhesive, 5: LED, 6: first PD, 7: second PD, 8: first grating baffle, 9: second grating baffle, 21: hot melt positioning column, 22: first terminal locating hole, 23: second terminal locating hole, 24: third terminal locating hole, 25: first PD through-slot, 26: second PD through-slot, 27: LED through-slot, 31: first light-transmitting window, 32: second light-transmitting window, 33: third light-transmitting window.

The same reference numeral is denoted to the same or similar feature or function throughout the drawings.

DETAILED DESCRIPTION

To solve the above-mentioned problems that the assembly manners of the existing barometers are complicated and the requirements for the terminal products are high, the present application provides a heart rate module, in which a PCB assembly, a rear housing and a light-transmitting cover plate are assembled into a module.

The specific embodiments of the present application will be described in more detail below with reference to the accompanying drawings.

Figure 2:
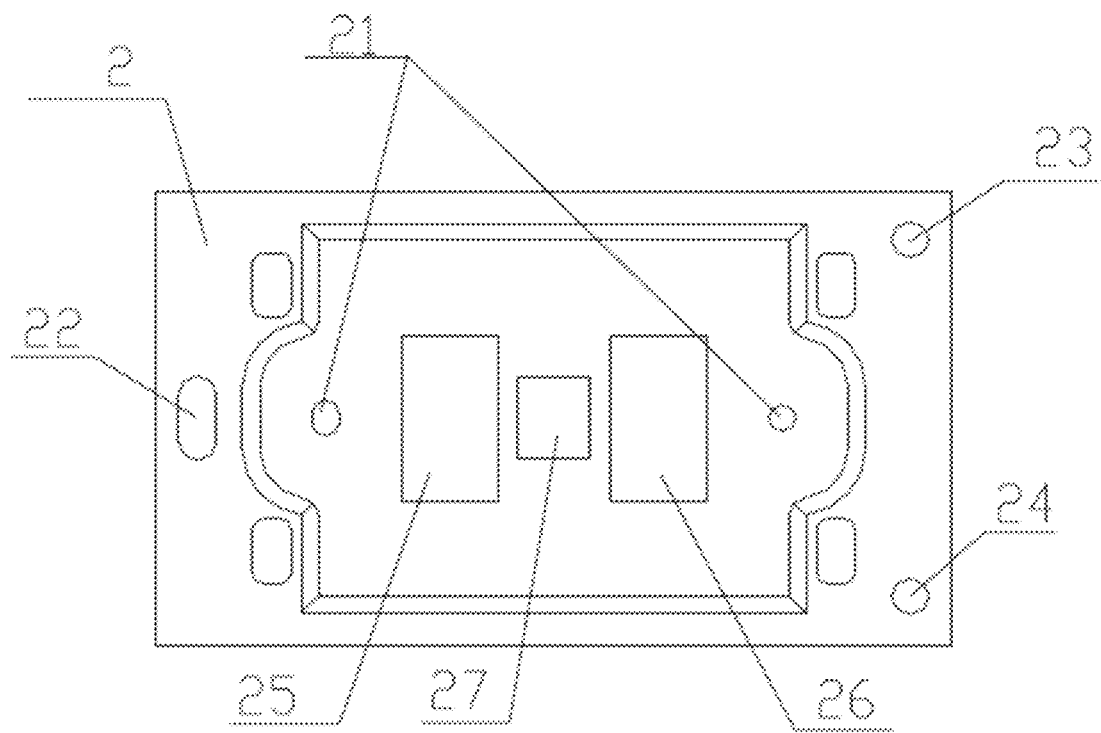
FIG. 2 is a structural schematic diagram of the rear housing according to the embodiment of the present application.
Figure 3:
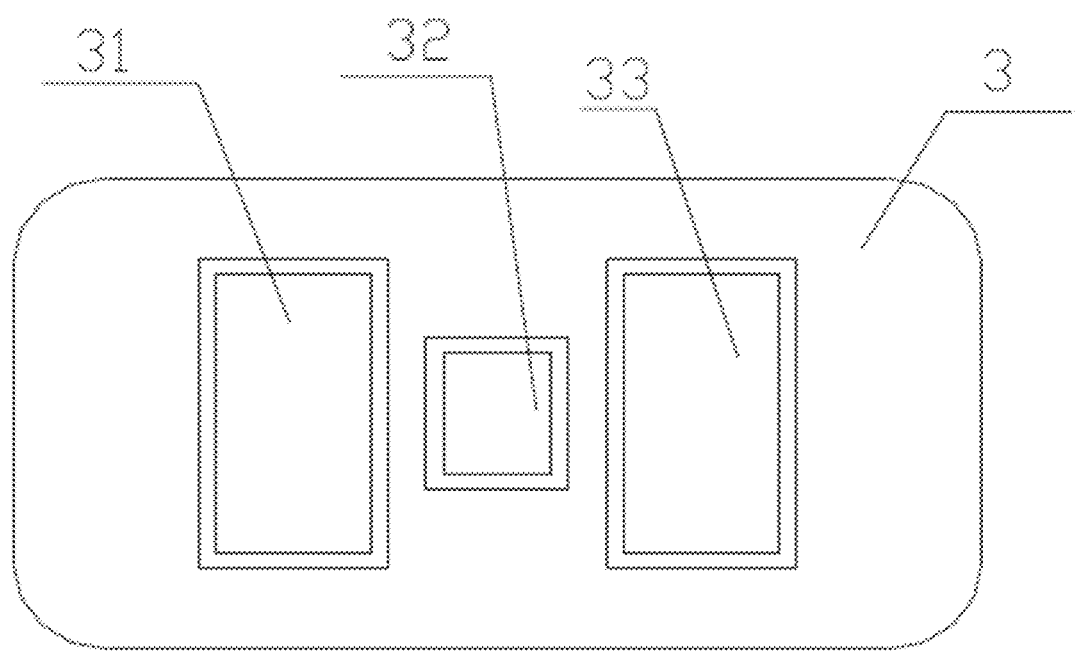
FIG. 3 is a top structural schematic diagram of the light-transmitting cover plate according to the embodiment of the present application.
Figure 4:
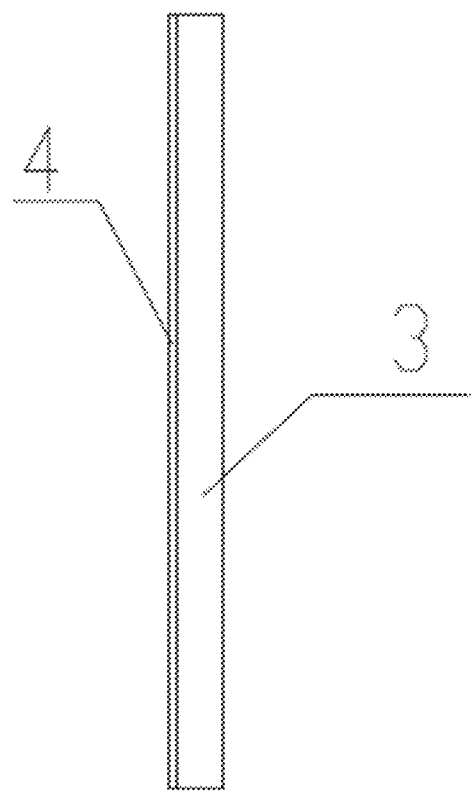
FIG. 4 is a side structural schematic diagram of the light-transmitting cover plate according to the embodiment of the present application.
Figure 5:
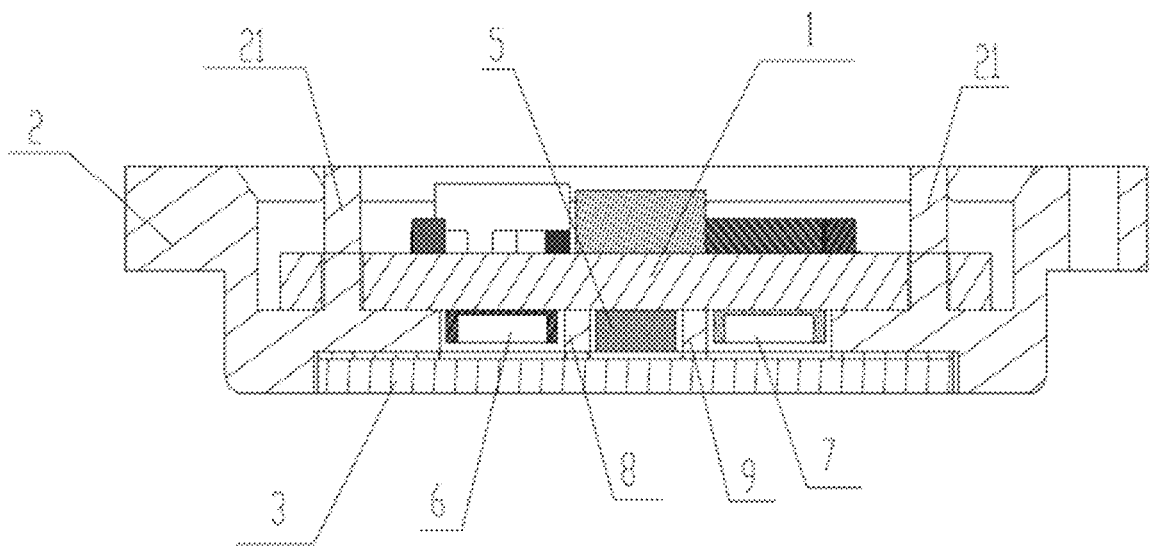
FIG. 5 is a cross-section structural schematic diagram of the heart rate module according to the embodiment of the present application.

In order to explain the structure of the heart rate module of the present application, FIG. 1 to FIG. 5 exemplarily illustrate the structure of the heart rate module from different angles, respectively. Specifically, FIG. 1 illustrates a exploded structure of the heart rate module according to the embodiment of the present application, FIG. 2 illustrates a structure of the rear housing according to the embodiment of the present application, FIG. 3 illustrates a top structure of the light-transmitting cover plate according to the embodiment of the present application, FIG. 4 illustrates a side structure of the light-transmitting cover plate according to the embodiment of the present application, and FIG. 5 illustrates a cross-section structure of the heart rate module according to the embodiment of the present application.

As shown in FIGS. 1 to 5, the heart rate module of the present application comprises a housing structure composed of a rear housing 2 and a light-transmitting cover plate 3, and a PCB assembly 1 is disposed in the housing structure.

The PCB assembly 1 includes a PCB, a first PD 6, a second PD 7 and an LED 5, wherein the first PD 6, the second PD 7 and the LED 5 are fixed on the PCB at a preset distance, hot melt positioning columns 21 are disposed on the rear housing 2, and the PCB assembly 1 is fixed on the rear housing 2 through the hot melt positioning columns 21.

The heart rate module is assembled in the following way: assembling the rear housing 2 and the light-transmitting cover plate 3 together to form the housing structure, keeping the tooling under pressure for a period of time to ensure good bonding; then assembling the PCB assembly 1 into the rear housing 2, two hot melt positioning columns 21 are provided on the rear housing 2, the hot melt positioning columns 21 pass through the PCB when assembling, and after the PCB assembly 1 is assembled and positioned, the two hot melt positioning columns 21 of the rear housing 2 are hot melted by a hot melt machine, thereby keeping the PCB assembly 1 and the rear housing 2 integrated.

That is, in the present application, the PCB assembly 1, the first PD 6, the second PD 7, the LED 5, the rear housing 2 and the light-transmitting cover plate 3 are integrated into a module, the distances of the first PD 6, the second PD 7, the LED 5 and the light-transmitting cover plate 3 are adjusted in the module and the algorithm is burned into the module to assemble into a semi-finished product. The terminal customers can directly assemble the module onto the product, without the need to design complex optical distances or structures, which is convenient for users to use.

In the embodiment of the present application, the PCB assembly 1 comprises elements such as a PCB, a first PD 6, a second PD 7, an LED 5 and a micro-control electronic device, wherein elements such as the first PD 6, the second PD 7, the LED 5 and the micro-control electronic device are each disposed and fixed on the PCB to integrate a module circuit.

The rear housing 2 supports the integration of the PCB assembly 1 and light-transmitting cover plate 3, and is provided with grating baffles thereon, which may prevent optical interference of each of the PD and LED, wherein a first grating baffle 8 and a second grating baffle 9 are used to prevent optical interferences of the first PD 6, the second PD 7 and the LED 5. A first PD through-slot 25 for accommodating the first PD 6, a second PD through-slot 26 for accommodating the second PD 7, and an LED through-slot 27 for accommodating the LED 5 are disposed on the rear housing 2, the three through-slots are separated from each other. The first grating baffle 8 and the second grating baffle 9 are formed between the three separated through-slots, and thus, the first grating baffle 8 and the second grating baffle 9 can prevent the optical interferences between the first PD 6 and the LED 5 and between the second PD 7 and the LED 5. Preferably, the length of each grating baffle in the thickness direction of the rear housing 2 is greater than or equal to the length of the PD and the LED on both sides thereof.

In the embodiment of FIG. 2, two hot melt positioning columns 21 are provided on the rear housing 2, which serve to guide when assembling the rear housing 2 with the PCB assembly 1 and to hot-melt and fix the PCB assembly 1 onto the rear housing 2. Since two locating holes matching with the two hot melt positioning columns 21 are disposed on the PCB of the PCB assembly 1, the PCB assembly 1 and the rear housing 2 can be well positioned and fixed.

The first PD through-slot 25, the second PD through-slot 26 and the LED through-slot 27 are provided on the rear housing 2, wherein the PD through-slot 25 is used to accommodate the first PD 6, the PD through-slot 26 is used to accommodate the second PD 7, and the LED through-slot 27 is used to accommodate the LED 5. The first PD through-slot 25 facilitates the light reception of the first PD 6, the second PD through-slot 26 facilitates the light reception of the second PD 7, and the LED through-slot 27 facilitates the light of the LED 5 outgoing.

Further, three terminal locating holes, i.e., a first terminal locating hole 22, a second terminal locating hole 23 and a third terminal locating hole 24, are provided on the rear housing 2, and the three terminal locating holes allow the heart rate module to be fixed and assembled with the terminal product.

The light-transmitting cover plate 3 is a transparent injection molding material, and preferably, has a light transmittance of more than 90%, and has a refractive index of more than 1.4. In the embodiment of FIG. 3 and FIG. 4, a black silk screen area is provided on a surface of the light-transmitting cover plate 3 (except for the area corresponding to that of the first PD through-slot 25, the second PD through-slot 26 and the LED through-slot 27), and windows without the black silk screen, which are called light-transmitting windows, are provided on the light-transmitting cover plate 3 at positions corresponding to that of the first PD, the second PD and the LED, including a first light-transmitting window 31, a second light-transmitting window 32 and a third light-transmitting window 33, wherein the first light-transmitting window 31 corresponds to the first PD 6, the second light-transmitting window 32 corresponds to the second PD 7, and the third light-transmitting window 33 corresponds to the LED 5, so as to facilitate the light reception of each PD and the light output of the LED.

In one optional embodiment, the light-transmitting cover plate 3 is fixed to the rear housing 2 by a double-sided adhesive 4. Specifically, in order to facilitate the assembly of the rear housing 2 with the light-transmitting cover plate 3, a layer of the double-sided adhesive 4 is disposed on the surface of the light-transmitting cover plate 3, and the double-sided adhesive may be provided at the edges of the three light-transmitting windows. The light-transmitting cover plate 3 is adhered to the rear housing 2 by the double-sided adhesive 4.

The module constituted with such design structure of the present application can maintain the distances between the PD, the LED and the light-transmitting cover plate, and combined with the algorithm thereof, the best performance in terms of structure can be adjusted to, and each grating can also ensure no light leakage during the operating, such that the performance of the heart rate meter won't be affected.

As can be seen from the above embodiment, in the heart rate module of the present application, the PCB assembly, the rear housing and the light-transmitting cover plate are assembled into one module, the module pre-sets the distances of the PD, the LED and the light-transmitting cover plate and is assembled into a semi-finished product, the terminal customers can directly assemble this module into a product, thereby improving the efficiency and yield of terminal customer design and production line assembly.

The heart rate module according to the present application has been described by way of example with reference to the accompanying drawings. However, those skilled in the art should understand that various improvements can be made to the above-described heart rate module of the present application without departing from the scope of the present application. Therefore, the scope of protection of the present application should be determined by the appended claims.

What is claimed is:

1. A heart rate module comprising a housing structure composed of a rear housing and a light-transmitting cover plate, wherein:
   a printed circuit board (PCB) assembly is disposed in the housing structure;
   the PCB assembly includes a PCB, a first photodiode (PD), a second PD, and a light emitting diode (LED), wherein the PDs and the LED are fixed on the PCB at a predetermined distance;
   a hot melt positioning column is disposed on the rear housing, and the PCB assembly is fixed on the rear housing through the hot melt positioning column;
   a plurality of through-slots are provided on the rear housing;
   each of the through-slots is used to accommodate one of the PDs or the LED;
   grating baffles for preventing optical interferences are respectively formed between the through-slots;
   the grating baffles comprise a first grating baffle preventing the optical interferences between the first PD and the LED and a second grating baffle preventing the optical interferences between the second PD and the LED; and
   a black silk screen is provided in an area other than a position corresponding to that of the PDs and the LED, on a surface of the light-transmitting cover plate, so as to form a light-transmitting window at the position corresponding to that of the PDs and the LED.

2. The heart rate module according to claim 1, wherein the PCB assembly further comprises a micro control-electronic device.

3. The heart rate module according to claim 1, wherein a locating hole is provided on the PCB, and corresponds to the hot melt positioning column on the rear housing.

4. The heart rate module according to claim 1, wherein a terminal locating hole is further provided on the rear housing, wherein the terminal locating hole is used for fixing and assembling with a terminal product.

5. The heart rate module according to claim 1, wherein the light-transmitting cover plate is fixed to the rear housing by a double-sided adhesive.

* * * * *